United States Patent
Mochizuki et al.

(10) Patent No.: US 9,703,928 B2
(45) Date of Patent: Jul. 11, 2017

(54) INFORMATION PROCESSING APPARATUS, METHOD, AND COMPUTER-READABLE STORAGE MEDIUM FOR GENERATING FOOD ITEM IMAGES

(75) Inventors: Daisuke Mochizuki, Chiba (JP); Tomohiko Gotoh, Kanagawa (JP); Tatsuhito Sato, Tokyo (JP); Shunsuke Mochizuki, Tokyo (JP); Yuki Okamura, Saitama (JP); Yun Sun, Tokyo (JP); Takeshi Yaeda, Tokyo (JP)

(73) Assignee: SONY CORPORATION, Tokyo (JP)

(*) Notice: Subject to any disclaimer, the term of this patent is extended or adjusted under 35 U.S.C. 154(b) by 218 days.

(21) Appl. No.: 13/484,730

(22) Filed: May 31, 2012

(65) Prior Publication Data
US 2013/0027424 A1 Jan. 31, 2013

(30) Foreign Application Priority Data
Jul. 26, 2011 (JP) .................................. 2011-162790

(51) Int. Cl.
*G09G 5/00* (2006.01)
*G06F 19/00* (2011.01)

(52) U.S. Cl.
CPC ...... *G06F 19/3406* (2013.01); *G06F 19/3475* (2013.01)

(58) Field of Classification Search
None
See application file for complete search history.

(56) References Cited

U.S. PATENT DOCUMENTS

| | | | |
|---|---|---|---|
| 2001/0000810 A1* | 5/2001 | Alabaster | 707/104 |
| 2002/0133378 A1* | 9/2002 | Mault | A61B 5/0002 705/3 |
| 2007/0146504 A1* | 6/2007 | Morimoto et al. | 348/231.3 |
| 2010/0173269 A1* | 7/2010 | Puri | G09B 19/0092 434/127 |
| 2010/0179864 A1* | 7/2010 | Feldman et al. | 705/12 |
| 2011/0182477 A1* | 7/2011 | Tamrakar | G06T 7/0002 382/110 |
| 2011/0318717 A1* | 12/2011 | Adamowicz | 434/127 |
| 2012/0094258 A1* | 4/2012 | Langheier et al. | 434/127 |
| 2012/0096405 A1* | 4/2012 | Seo | G06F 3/04886 715/825 |

FOREIGN PATENT DOCUMENTS

JP 2004-118562 4/2004

OTHER PUBLICATIONS

U.S. Appl. No. 13/549,903, filed Jul. 16, 2012, Sato, et al.

* cited by examiner

*Primary Examiner* — Barry Drennan
*Assistant Examiner* — Khoa Vu
(74) *Attorney, Agent, or Firm* — Oblon, McClelland, Maier & Neustadt, L.L.P.

(57) ABSTRACT

An information processing apparatus includes a clipping section that clips, from a captured image in which a food is captured as a subject, regions for each food to generate food images, and a grouping section that groups the generated food images for each identical subject.

14 Claims, 12 Drawing Sheets

FIG. 4A  CAPTURED IMAGES
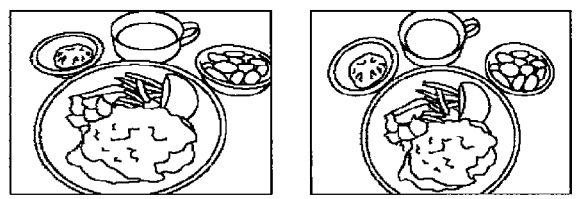
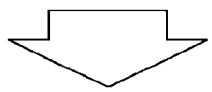
FIG. 4B  FOOD IMAGES
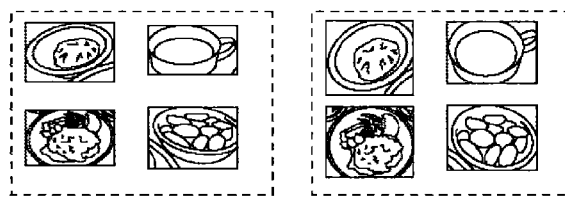
FIG. 4C
GROUP
FIG. 4D  REPRESENTATIVE FOOD IMAGES

| < PREVIOUS MONTH | | | | | | NEXT MONTH > |
|---|---|---|---|---|---|---|
| CALORIES (kcal) TAKEN IN APRIL 2011 | | | | | | |
| MON | TUE | WED | THU | FRI | SAT | SUN |
|  |  |  |  | 1<br>1450 | 2<br>1600 | 3<br>1470 |
| 4<br>1520 | 5<br>1340 | 6<br>1540 | 7<br>1630 | 8<br>1700 | 9<br>1630 | 10<br>980 |
| 11<br>1560 | 12<br>1770 | 13<br>1640 | 14<br>1780 | 15<br>1690 | 16<br>1500 | 17<br>1990 |
| 18 | 19 | 20 | 21 | 22 | 23 | 24 |

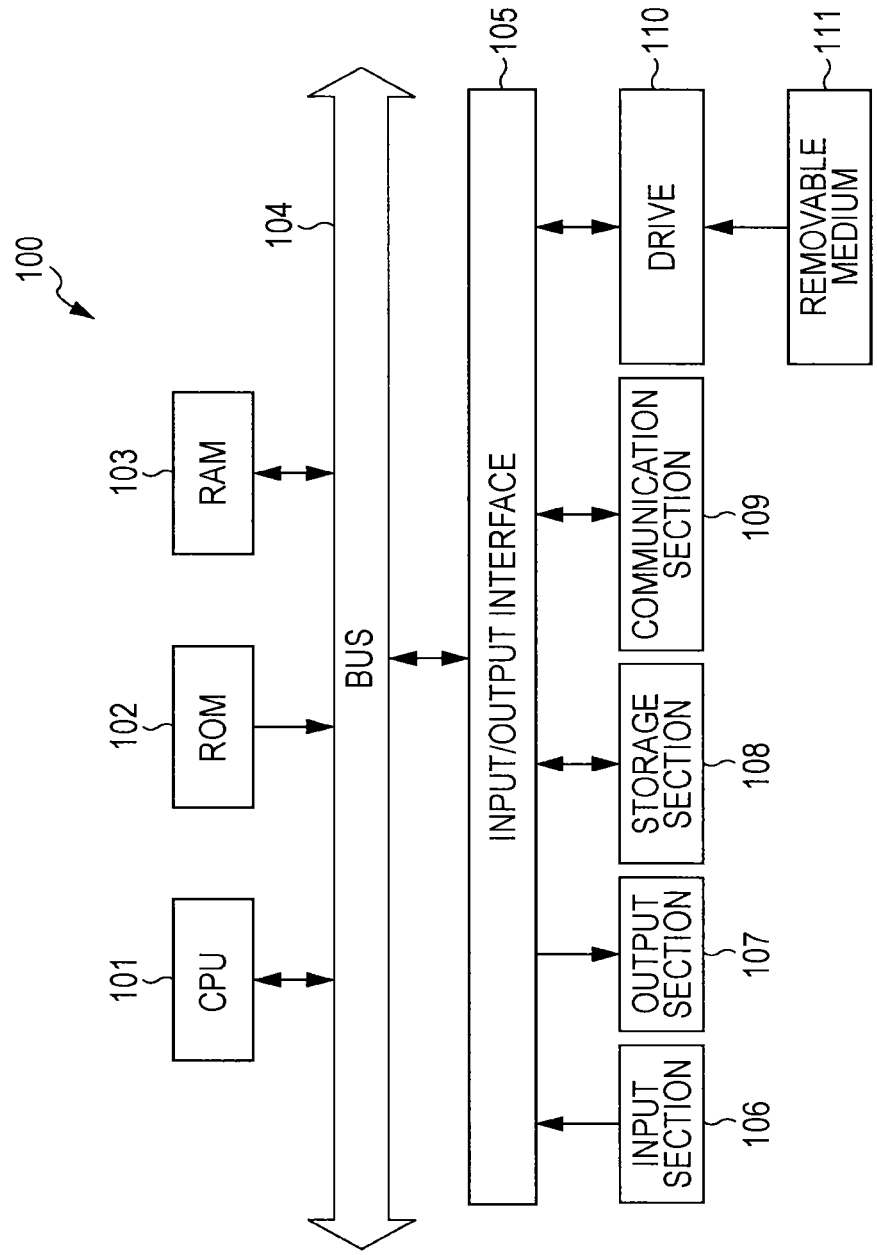

INFORMATION PROCESSING APPARATUS, METHOD, AND COMPUTER-READABLE STORAGE MEDIUM FOR GENERATING FOOD ITEM IMAGES

CROSS-REFERENCE TO RELATED APPLICATION

The present disclosure contains subject matter related to that disclosed in Japanese Priority Patent Application JP 2011-162790 filed in the Japan Patent Office on Jul. 26, 2011, the entire contents of which are hereby incorporated by reference.

BACKGROUND

The present disclosure relates to an information processing apparatus, an information processing method, and a program, and in particular to an information processing apparatus, an information processing method, and a program that allows dietary information on a user to be managed on the basis of an image in which a food eaten by the user is captured.

Hitherto, there have been systems that can indicate the number of calories of a food eaten in an eating establishment. In such systems, a user captures an image of the food served in the eating establishment using a portable terminal equipped with a camera to send the image of the food and information on the eating establishment to a predetermined server, and then information such as the amount of calorie intake is sent from the server to the portable terminal of the user (see Japanese Unexamined Patent Application Publication No. 2004-118562, for example).

SUMMARY

In the systems discussed above, the server stores for each eating establishment a table in which foods served by the eating establishment and the respective numbers of calories are correlated. Thus, information such as the number of calories may not be obtained for a food served by the eating establishment but not contained in the table or a food prepared at home.

In capturing an image of a food served, in addition, it is assumed that a plurality of images may be captured for an identical subject (food). In the systems discussed above, it is necessary for the user to select which of the plurality of obtained images is to be sent to the server. In this case, the user may not necessarily be able to select an image that is suitable for determination of the amount of calorie intake.

Further, if the user does not select one of a plurality of images in which an identical subject (food) is captured, the systems may consider that he/she has eaten a plurality of times the food which he/she has actually eaten only once, and may erroneously determine the amount of calorie intake.

It is therefore desirable to provide accurate dietary information such as the amount of calorie intake to a user.

According to an embodiment of the present disclosure, there is provided an information processing apparatus including a clipping section that clips, from a captured image in which a food is captured as a subject, regions for each food to generate food images, and a grouping section that groups the generated food images for each identical subject.

The information processing apparatus according to the embodiment of the present disclosure may further include a selection section that selects a representative food image from each group of the food images grouped for each identical subject, a nutrition determination section that analyzes the selected representative food image to determine on the basis of analysis results at least one of a number of calories and a nutrient balance of the food captured as the subject of the representative food image, and a presentation section that presents to a user results of the determination made by the nutrition determination section.

The selection section may select the representative food image, which is suitable for the determination to be made by the nutrition determination section, from each group of the food images grouped for each identical subject.

The selection section may select the representative food image from each group of the food images grouped for each identical subject in accordance with an operation performed by the user.

The grouping section may pair all the generated food images to group the food images for each identical subject on the basis of results of determination as to whether or not two food images forming each pair have an identical subject.

The grouping section may pair all the generated food images, and may determine that two food images forming each pair do not have an identical subject in the case where respective dates and times of capture of the two food images or respective locations of capture of the two food images are apart from each other by more than a predetermined threshold.

The clipping section may clip from the captured image regions for a piece of tableware on which each food is served to generate the food images.

The information processing apparatus according to the present disclosure may further include an image capturing section that captures an image of a food as a subject to generate the captured image.

According to another embodiment of the present disclosure, there is provided an information processing method including an information processing apparatus clipping, from a captured image in which a food is captured as a subject, regions for each food to generate food images, and the information processing apparatus grouping the generated food images for each identical subject.

According to still another embodiment of the present disclosure, there is provided a program that causes a computer to function as a clipping section that clips, from a captured image in which a food is captured as a subject, regions for each food to generate food images, and a grouping section that groups the generated food images for each identical subject.

According to the embodiments of the present disclosure, regions for each food are clipped from a captured image in which a food is captured as a subject to generate food images, and the generated food images are grouped for each identical subject.

According to the embodiments of the present disclosure, accurate dietary information such as the amount of calorie intake can be provided.

BRIEF DESCRIPTION OF THE DRAWINGS

FIGS. 4A to 4D show examples of captured images etc. to be used in the dietary management process;

FIG. 15 is a block diagram showing an exemplary configuration of a computer.

DETAILED DESCRIPTION OF EMBODIMENTS

An embodiment of the present disclosure will be described in detail below with reference to the drawings.

1. Embodiment

Exemplary Configuration of Dietary Management System

Figure 1:
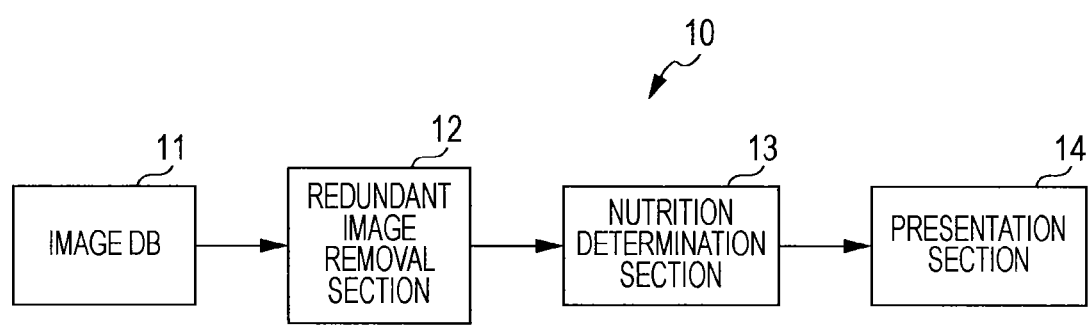
FIG. 1 is a block diagram showing an exemplary configuration of a dietary management system according to an embodiment of the present disclosure.

FIG. 1 shows an exemplary configuration of a dietary management system according to an embodiment of the present disclosure. A dietary management system 10 includes an image database (DB) 11, a redundant image removal section 12, a nutrition determination section 13, and a presentation section 14.

The image database 11 stores a plurality of captured images (hereinafter referred to as a "collection of captured images") in which a food to be eaten is captured as a subject by a user. Attribute information including the date and time of capture, the location of capture (such as latitude and longitude), or the like is added to each captured image. The captured images may be obtained by capturing a plurality of foods served on a plurality of pieces of tableware such as dishes and bowls in a single image, or may be obtained by capturing the plurality of foods individually for each piece of tableware. An identical subject (food) may be captured redundantly in a plurality of captured images. A still image captured from a moving image may be used as a captured image.

The redundant image removal section 12 clips regions for each food from the captured images stored in the image database 11 to generate food images. The redundant image removal section 12 groups a plurality of food images in which an identical subject is captured to select a single representative food image from each group of food images.

The nutrition determination section 13 performs an image analysis on the representative food image selected from each group of food images to specify the food and the amount of the food on the basis of the analysis results. The nutrition determination section 13 further determines the number of calories, the nutritional value, or the like of the specified food on the basis of a correspondence table stored in advance in which foods and the number of calories, the nutritional value, or the like of the foods are correlated with each other.

The presentation section 14 presents to the user dietary information on the user, such as food items eaten by the user during a predetermined unit period (such as one day, one week, or one month), the number of calories, the nutritional value, and so forth, on the basis of the results of the determination made by the nutrition determination section 13.

Figure 2:
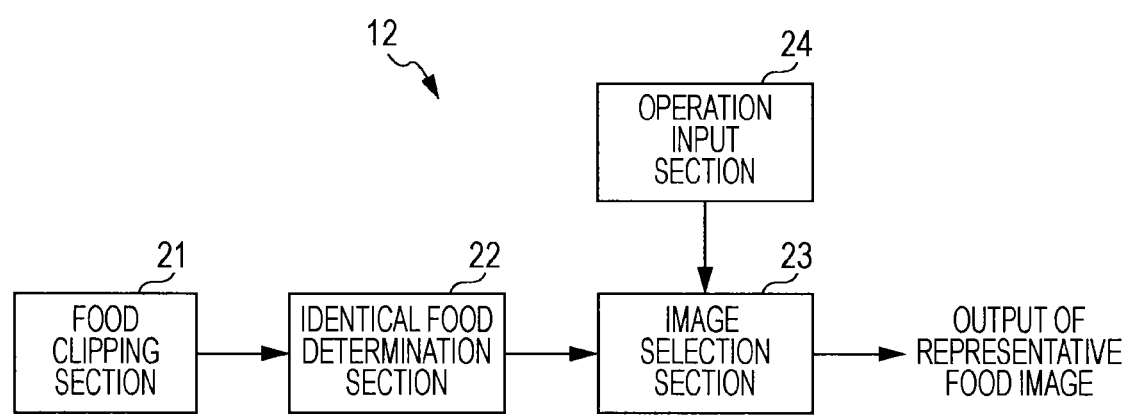
FIG. 2 is a block diagram showing an exemplary configuration of a redundant image removal section of FIG. 1.

FIG. 2 shows a detailed exemplary configuration of the redundant image removal section 12. The redundant image removal section 12 includes a food clipping section 21, an identical food determination section 22, an image selection section 23, and an operation input section 24.

The food clipping section 21 acquires the plurality of captured images stored in the image database 11, and clips regions for each food from each captured image to generate food images. Specifically, it is assumed that each food is served on a piece of tableware, and that the piece of tableware has a rectangular, circular, or oval shape. Thus, regions in which a rectangular, circular, or oval piece of tableware is captured are clipped from the captured images to generate food images.

Rather than by clipping regions in which a piece of tableware is captured as discussed above, food images may be generated on the basis of the color components and the texture characteristics of the food itself.

The identical food determination section 22 pairs all the food images with other food images to determine whether or not two food images forming each pair have an identical subject (food). An existing algorithm for calculating the similarity between images may be used in this determination.

In the case where the respective dates and times of capture of (the original captured images of) two similar food images forming a pair are apart from each other by a predetermined time or more, or in the case where the respective locations of capture of (the original captured images of) two similar food images forming a pair are apart from each other by a predetermined distance or more, it is highly likely that the same food is eaten on separate occasions, rather than on a single occasion. Thus, calculation of the similarity may be omitted, and it may be determined that the two food images do not have an identical subject (food).

The identical food determination section 22 further groups food images in which an identical subject is captured on the basis of the results of the determinations made for all the pairs.

The image selection section 23 selects a single representative food image from a plurality of food images belonging to each group. Specifically, an evaluation value is set using as a criterion whether the evaluation value allows the nutrition determination section 13 to accurately determine the type and the amount of the food in the subsequent stage, and a food image with the highest evaluation value is selected as the representative food image. Examples of the evaluation value are mentioned below.

(1) A food image in which a larger amount of food is left in the tableware allows more accurate determination of the amount of the food eaten, and thus is evaluated more highly.

(2) A food image in which a food is captured from a position closer to right above the food allows more accurate determination of the type of the food and the amount of the food eaten, and thus is evaluated more highly.

(3) In the case where the user dines with a plurality of persons, it is considered that a food positioned closer to the user is more likely to be eaten by the user rather than by the other persons. Thus, a food image in which a food placed on the side of the user (image capturer) in the captured image is captured is evaluated more highly.

(4) A food image in which a food is captured with less hindrance allows more accurate determination of the type of the food and the amount of the food eaten, and thus is evaluated more highly.

(5) A food image captured under more appropriate capturing conditions with neither too much nor too little exposure allows more accurate determination of the type of the food, and thus is evaluated more highly.

The operation input section 24 receives an operation input by the user. That is, the operation input section 23 presents the representative food image selected by the image selection section 23 to the user to allow the user to make a correction. Rather than the image selection section 23 selecting the representative food image on the basis of the evaluation values as discussed above, food images belonging to the same group may be presented to the user to allow the user to select the representative food image.

[Operation]

Next, a dietary management process performed by the dietary management system 10 will be described.

Figure 3:
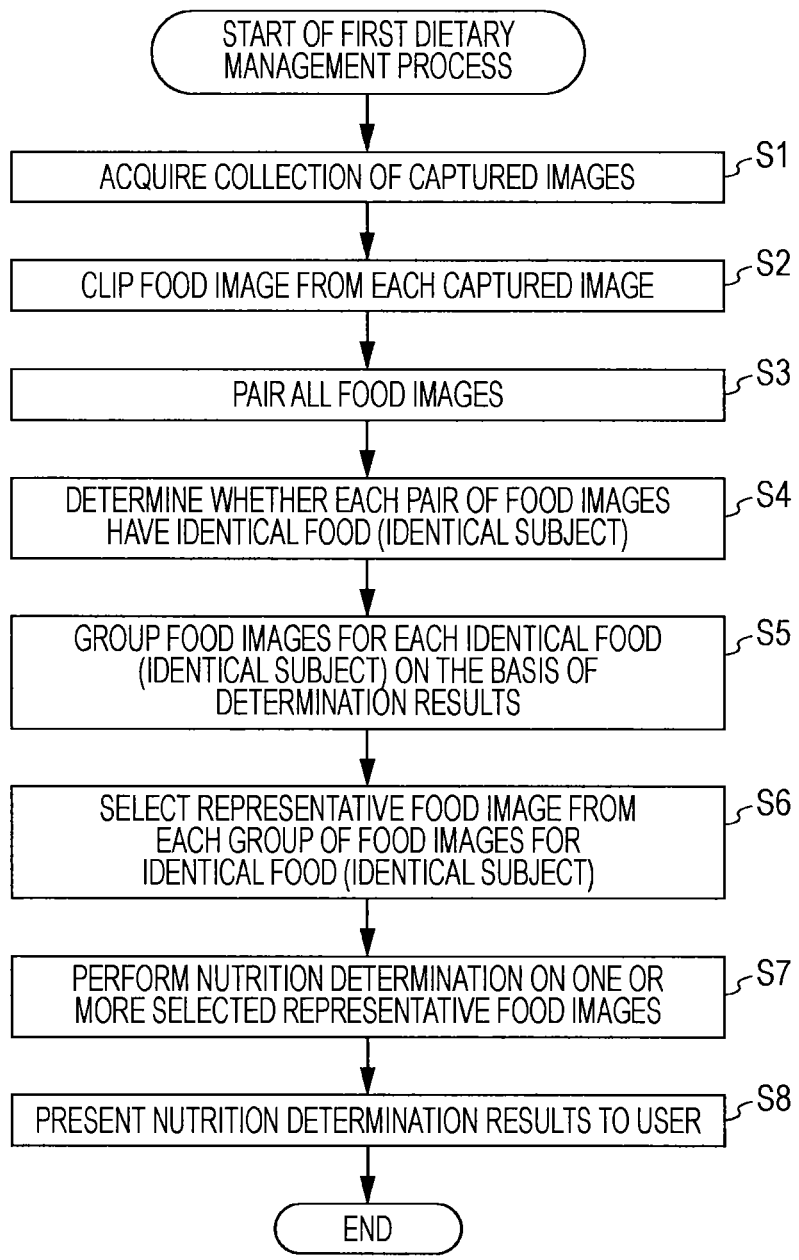
FIG. 3 is a flowchart illustrating a first dietary management process.

FIG. 3 is a flowchart illustrating a first dietary management process. FIGS. 4A to 4D show captured images etc. to be used in the process.

As a precondition for the dietary management process, the image database 11 already stores a plurality of captured images (a collection of captured images) obtained by capturing foods eaten by the user.

In step S1, the redundant image removal section 12 acquires a collection of captured images such as those shown in FIG. 4A from the image database 11. In step S2, the food clipping section 21 of the redundant image removal section 12 clips regions for each food from each captured image of the collection of captured images to generate food images such as those shown in FIG. 4B.

In step S3, the identical food determination section 22 pairs all the food images with other food images. In step S4, the identical food determination section 22 determines whether or not two food images forming each pair have an identical subject (food). In step S5, the identical food determination section 22 groups food images in which an identical subject is captured as shown in FIG. 4C on the basis of the results of the determinations made for all the pairs.

In step S6, the image selection section 23 selects a single representative food image from a plurality of food images belonging to each group as shown in FIG. 4D. In step S7, the nutrition determination section 13 performs an image analysis on the representative food image selected from each group of food images to specify the food and the amount of the food on the basis of the analysis results. The nutrition determination section 13 further determines the number of calories, the nutritional value, or the like of the specified food on the basis of a correspondence table stored in advance in which foods and the number of calories, the nutritional value, or the like of the foods are correlated with each other.

Figure 5:
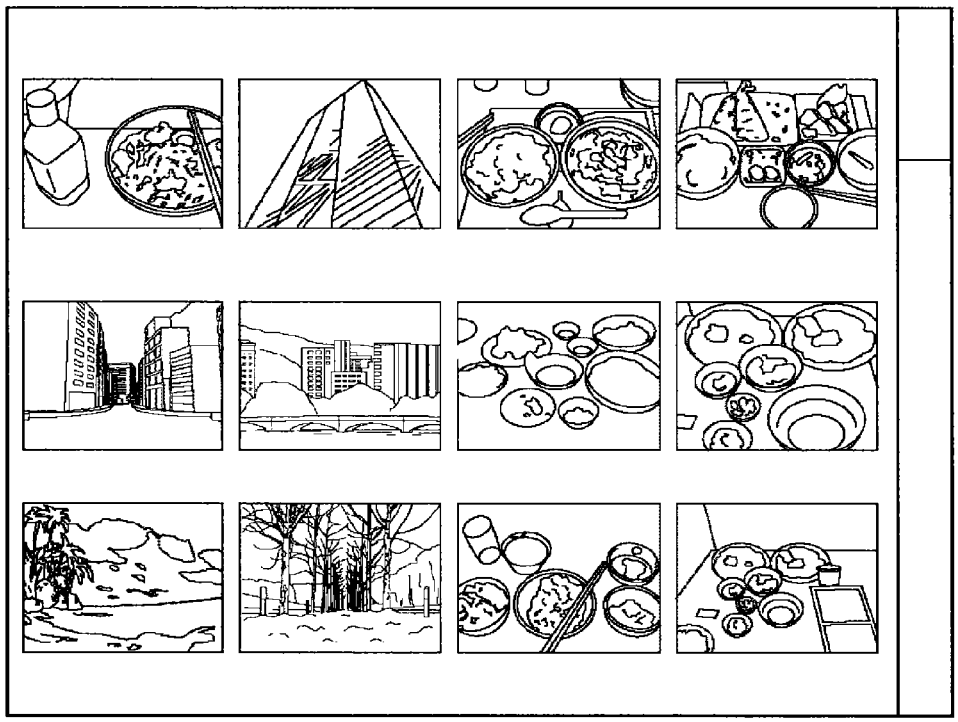
FIG. 5 shows an exemplary screen displayed by a presentation section.
Figure 6:
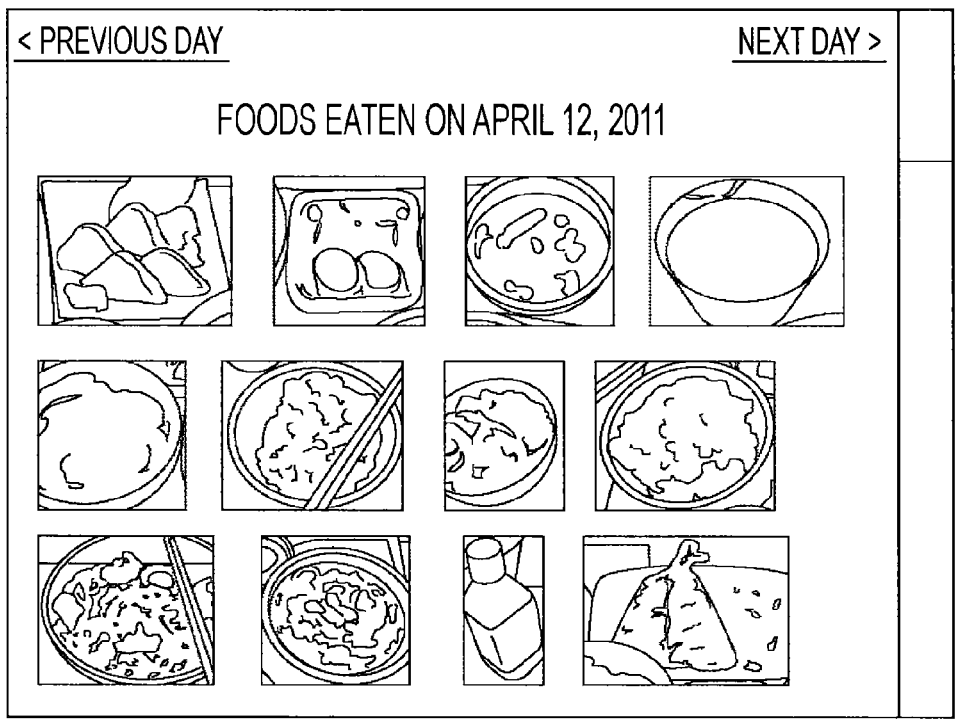
FIG. 6 shows an exemplary screen displayed by the presentation section.
Figures 7, 8:
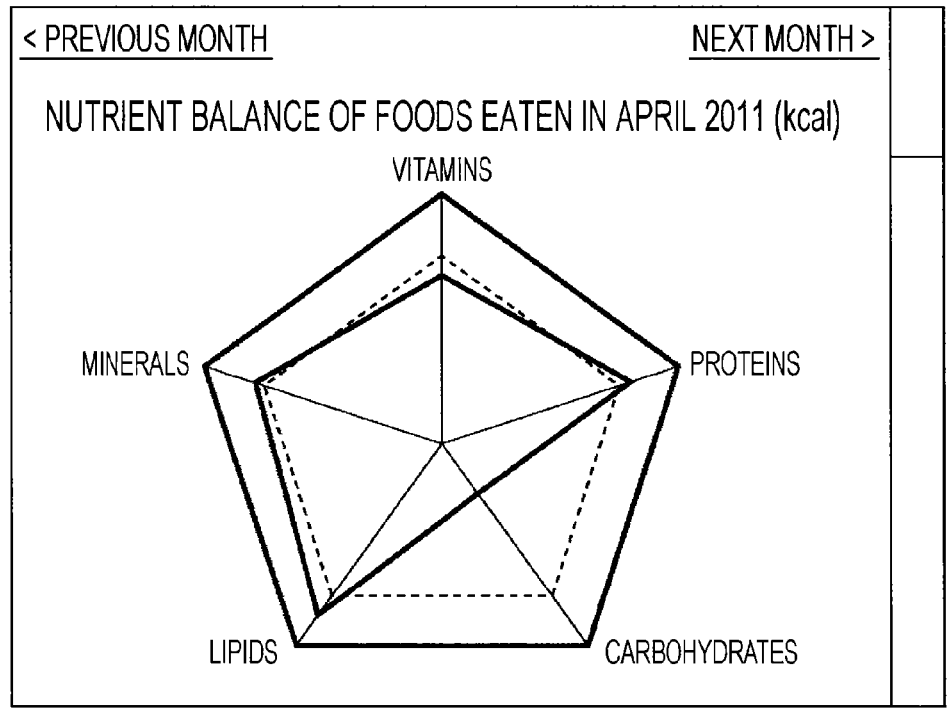
FIG. 7 shows an exemplary screen displayed by the presentation section.
FIG. 8 shows an exemplary screen displayed by the presentation section.

In step S8, the presentation section 14 presents to the user dietary information on the user on the basis of the results of the determination made by the nutrition determination section 13. Specifically, for example, the presentation section 14 may display a list of captured images to be processed as shown in FIG. 5, display a list of food images capturing foods eaten during one day as shown in FIG. 6, display a list of the amounts of calorie intake for each day of one month as shown in FIG. 7, or display the nutrient balance of foods taken during one month as shown in FIG. 8. The unit period for listed display may be changed as desired to one day, one week, one month, or the like. The nutrient balance may include elements other than vitamins, proteins, carbohydrates, lipids, and minerals shown in the drawing. The presentation section 14 may also present categorized display for staples, main dishes, relishes, dairy products, fruits, and so forth.

The first dietary management process has been described above.

In the first dietary management process, food images are clipped directly from captured images. However, similar captured images may be grouped to select one captured image so that a food image is clipped from the selected captured image.

Figure 9:
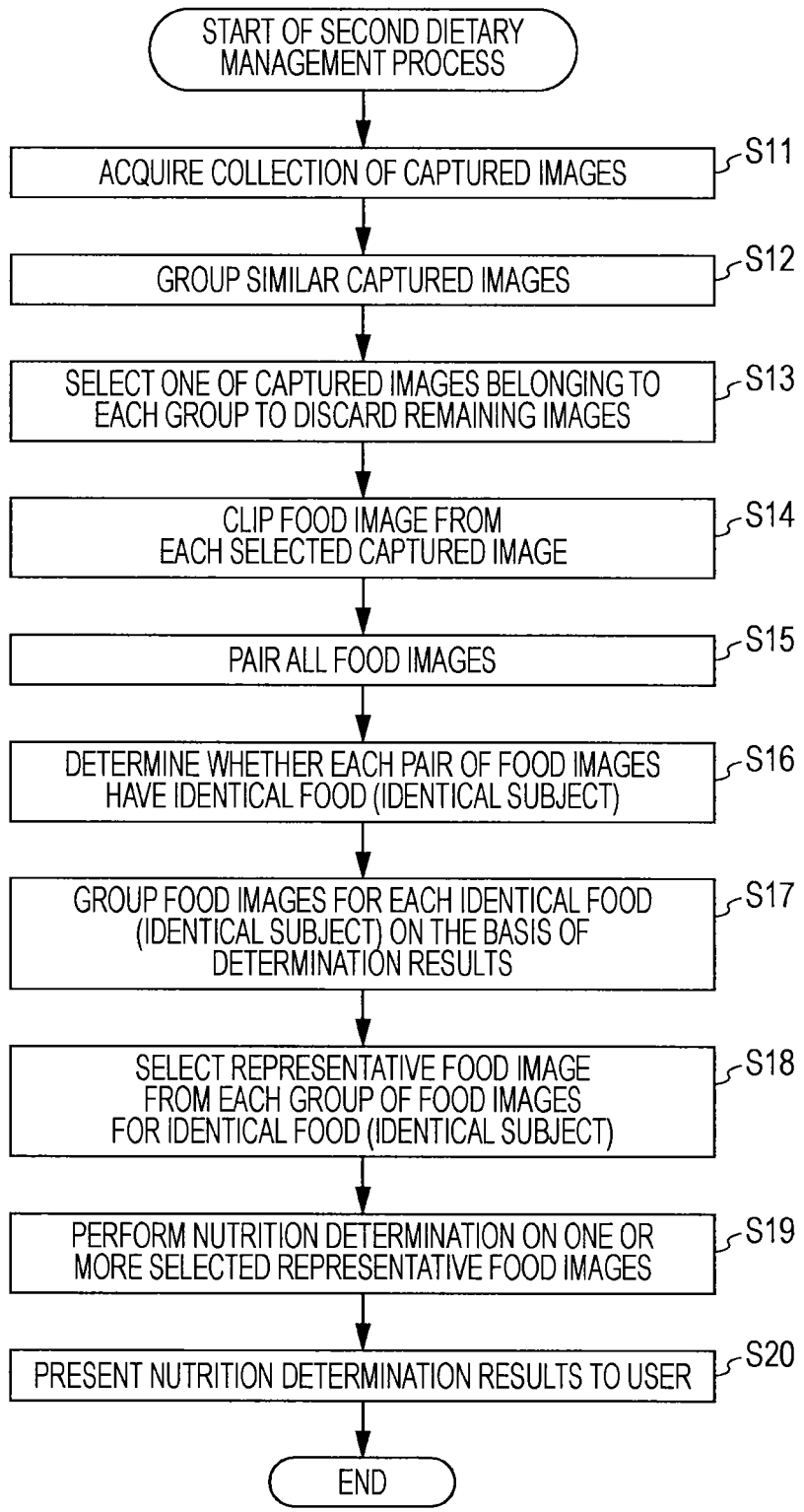
FIG. 9 is a flowchart illustrating a second dietary management process.

FIG. 9 is a flowchart illustrating a second dietary management process obtained by changing the first dietary management process as discussed above.

Also as a precondition for the second dietary management process, the image database 11 already stores a plurality of captured images (a collection of captured images) obtained by capturing foods eaten by the user.

In step S11, the redundant image removal section 12 acquires a collection of captured images such as those shown in FIG. 4A from the image database 11. In step S12, the identical food determination section 22 of the redundant image removal section 12 groups the captured images of the collection of captured images such that similar captured images belong to the same group. In step S13, the image selection section 23 selects one of a plurality of captured images belonging to each group of captured images to discard the remaining images. This selection is made using the same criterion as that used in the selection made in step S6 of the first dietary management process discussed above.

Steps S14 to S20 are the same as steps S2 to S8, respectively, of the first dietary management process discussed above, and thus are not described here. According to the second dietary management process described above, the number of captured images can be reduced in a stage before food images are clipped.

[Modifications]

In the exemplary configuration of the dietary management system 10 shown in FIG. 1, the arrangement of the constituent elements is not mentioned. The constituent elements may be disposed discretely.

FIGS. 10 to 13 each show an exemplary arrangement in which the constituent elements of the dietary management system 10 are disposed discretely.

Figure 10:
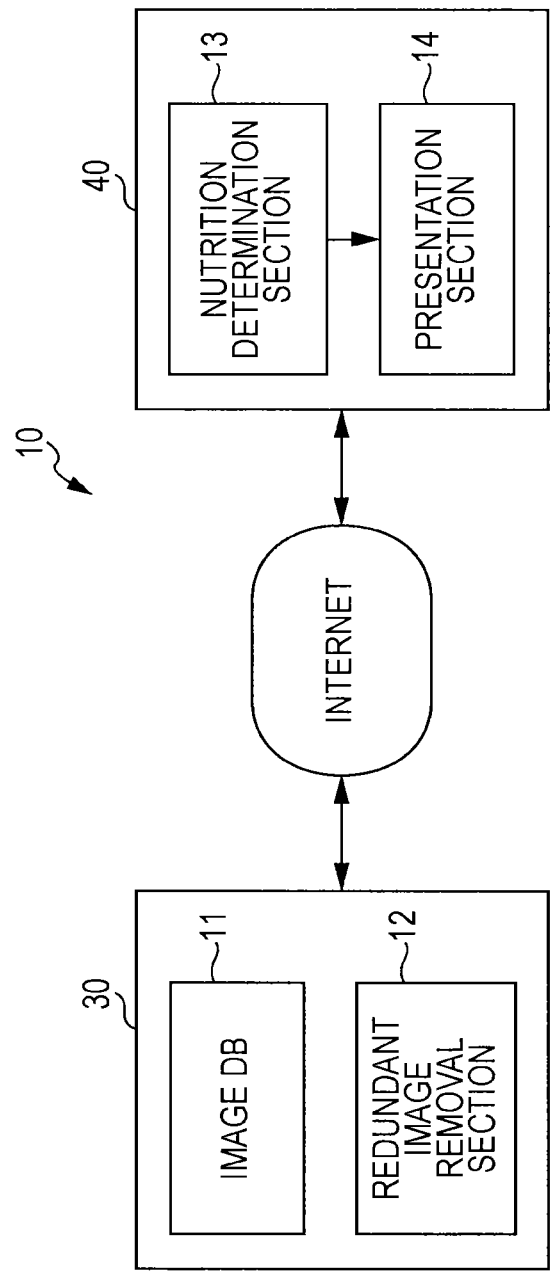
FIG. 10 is a block diagram showing an exemplary arrangement in which elements of the dietary management system are disposed discretely.

In the case of FIG. 10, the dietary management system 10 is formed by a user terminal 30 and a server 40 connected to each other via the Internet. The user terminal 30 is provided with the image database 11 and the redundant image removal section 12. The server 40 is provided with the nutrition determination section 13 and the presentation section 14.

Figure 11:
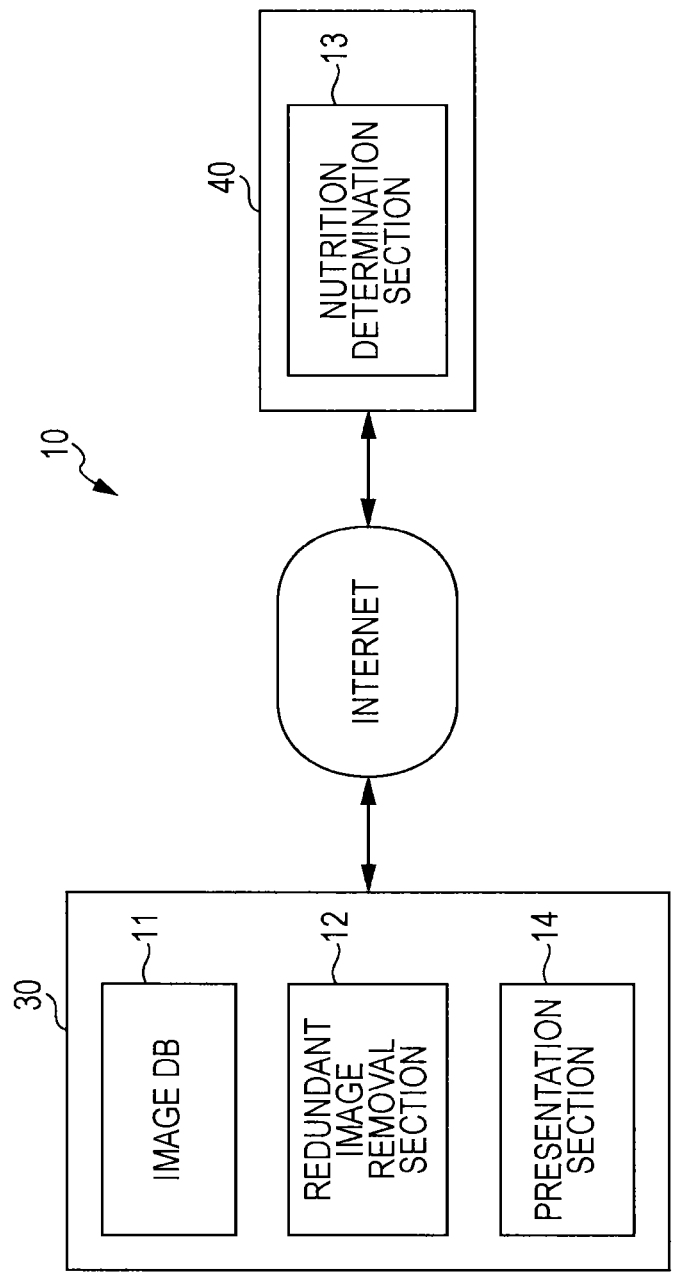
FIG. 11 is a block diagram showing an exemplary arrangement in which the elements of the dietary management system are disposed discretely.

In the case of FIG. 11, the dietary management system 10 is formed by a user terminal 30 and a server 40 connected to each other via the Internet. The user terminal 30 is provided with the image database 11, the redundant image removal section 12, and the presentation section 14. The server 40 is provided with the nutrition determination section 13.

Figure 12:
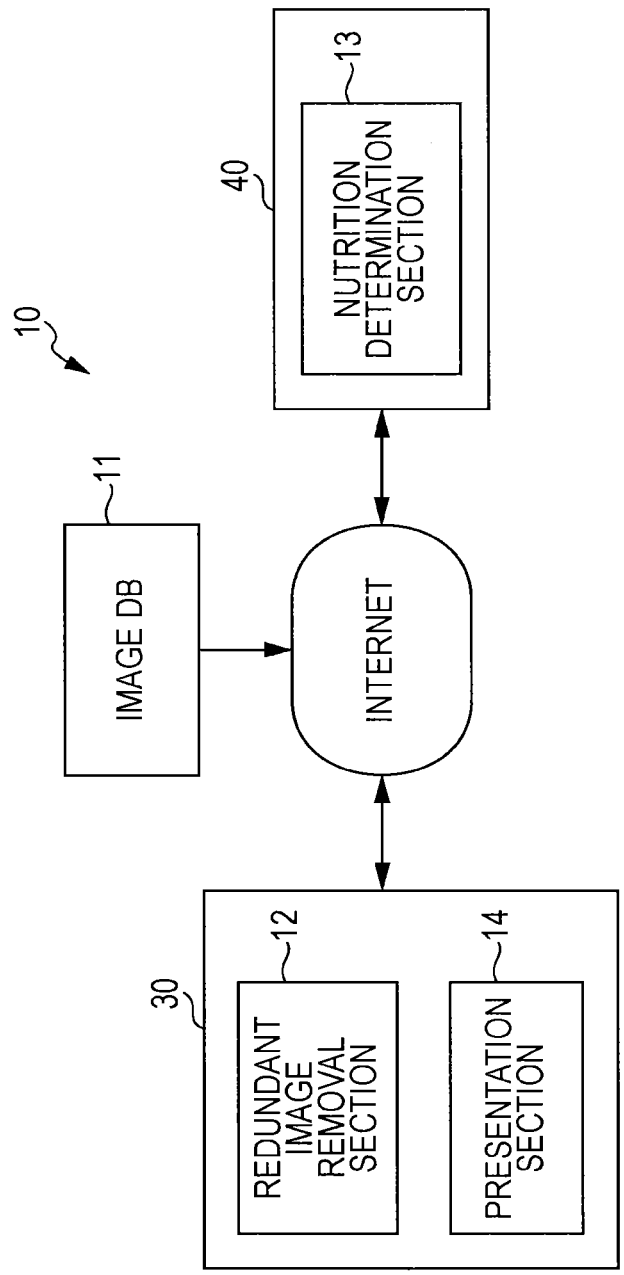
FIG. 12 is a block diagram showing an exemplary arrangement in which the elements of the dietary management system are disposed discretely.

In the case of FIG. 12, the dietary management system 10 is formed by a user terminal 30 and a server 40 connected to each other via the Internet. The image database 11 is provided on the Internet. The user terminal 30 is provided with the redundant image removal section 12 and the presentation section 14. The server 40 is provided with the nutrition determination section 13.

Figure 13:
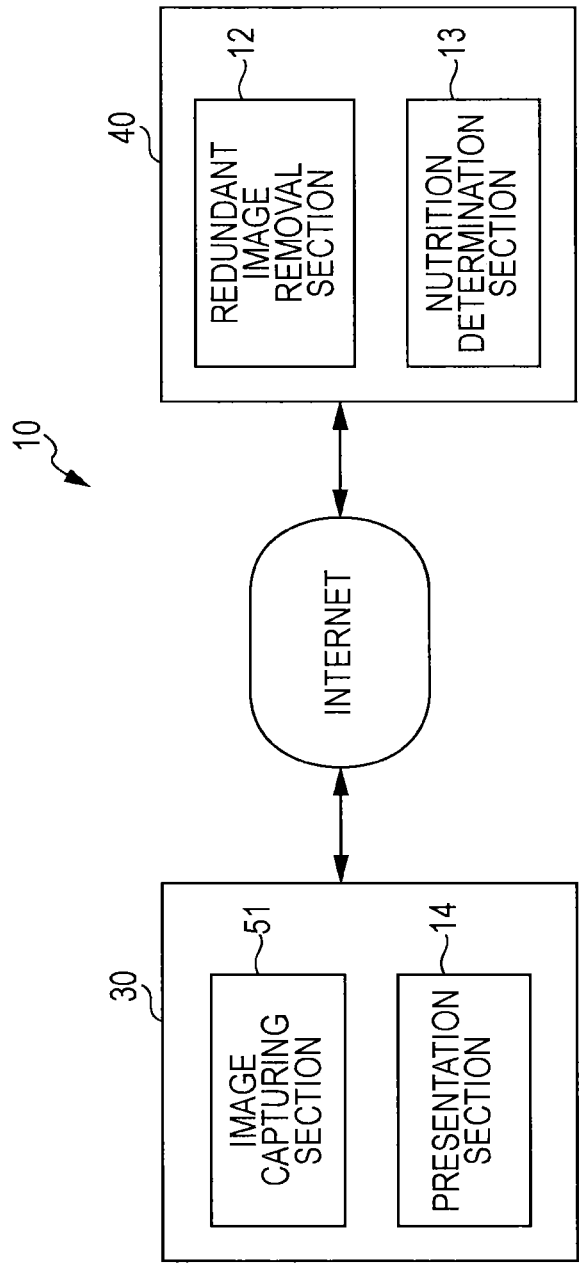
FIG. 13 is a block diagram showing an exemplary arrangement in which the elements of the dietary management system are disposed discretely.

In the case of FIG. 13, the dietary management system 10 is formed by a user terminal 30 and a server 40 connected to each other via the Internet. The user terminal 30 is provided with an image capturing section 51 and the presentation section 14. The server 40 is provided with the redundant image removal section 12 and the nutrition determination section 13.

Providing the user terminal 30 with the image capturing section 51 as shown in FIG. 13 makes it possible to dispense with the image database 11, and enables a real-time dietary management process in which an image of a food being eaten is captured at any time for real-time analysis and presentation of the amount of calorie intake, the nutrient balance, or the like to the user.

Figure 14:
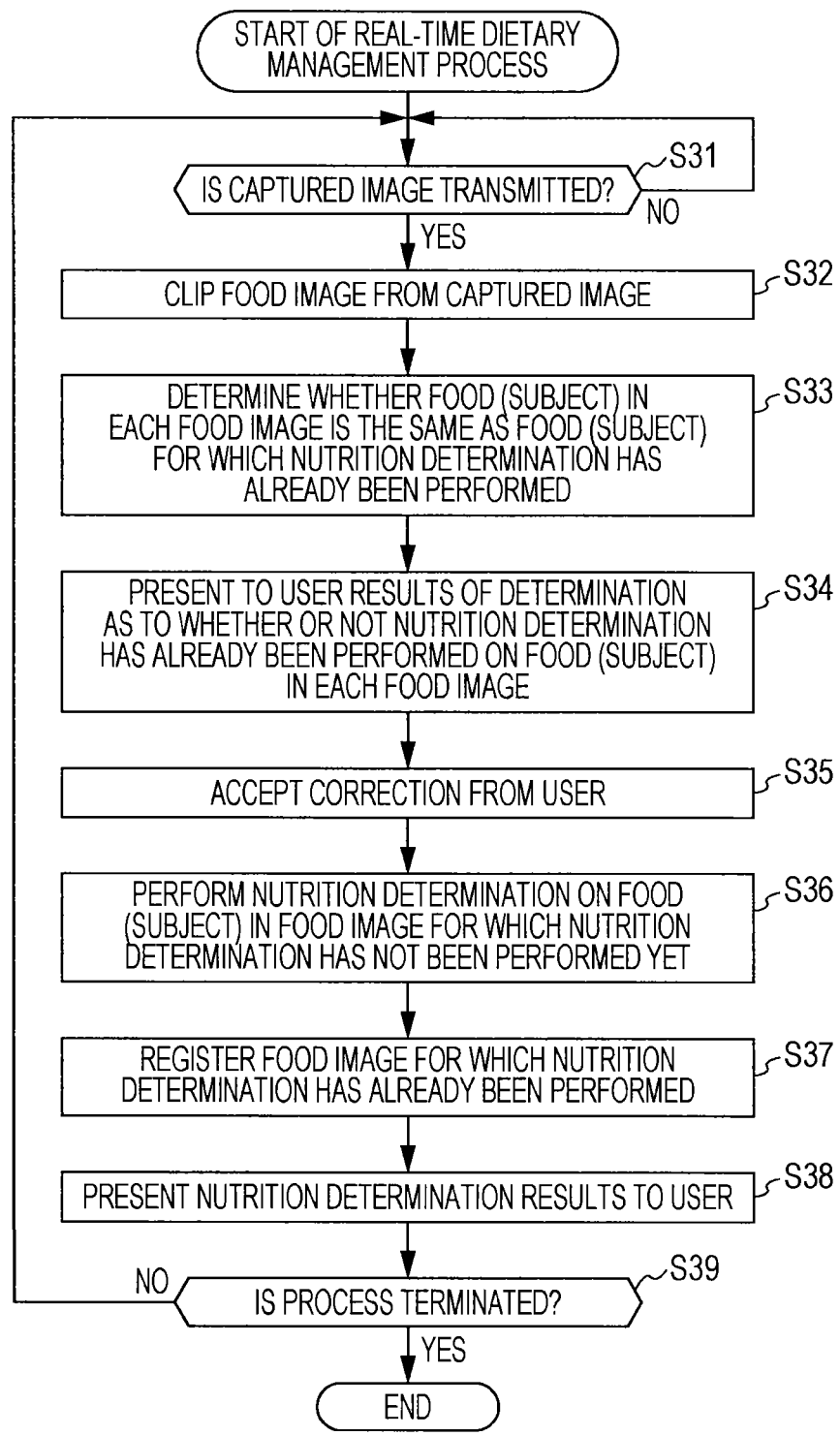
FIG. 14 is a flowchart illustrating a real-time dietary management processing.

FIG. 14 is a flowchart illustrating the real-time dietary management process performed by the dietary management system 10 shown in FIG. 13.

The real-time dietary management process is assumed to be executed concurrently with the user dining, and started in response to a predetermined operation performed on the user terminal 30. The user captures an image of a food to be eaten utilizing the image capturing section 51 of the user terminal 30. The captured image is transmitted to the server 40 via the Internet.

In step S31, the redundant image removal section 12 of the server 40 stands by until the captured image is transmitted from the user terminal 30. When the captured image is transmitted, the process proceeds to step S32. In step S32, the food clipping section 21 of the redundant image removal section 12 clips regions for each food from the captured image to generate food images.

In step S33, the identical food determination section 22 determines for each food image clipped in step S32 whether or not the subject (food) of the food image is the same as a food image for which nutrition determination has already been performed. In step S34, the determination results are sent to the user terminal 30. The presentation section 14 of the user terminal 30 presents to the user the results of determination as to whether or not the subject (food) of the food image clipped from the captured image is the same as a food image for which nutrition determination has already been performed. In step S35, the presentation section 14 of the user terminal 30 accepts from the user an operation to correct what is presented to the user to send the operation to the server 40. For example, in the case where an additional order is placed so that the same food is eaten twice or more, it is determined that the subject (food) of the food image is the same as a food image for which nutrition determination has already been performed. In this case, however, the user corrects the determination results such that it is determined that the subject (food) of the food image is different from a food image for which nutrition determination has already been performed.

In step S36, the nutrition determination section 13 performs an image analysis on the food image for which it is determined that nutrition determination has not been performed yet to specify the food and the amount of the food on the basis of the analysis results. The nutrition determination section 13 further determines the number of calories, the nutritional value, or the like of the specified food on the basis of a correspondence table stored in advance in which foods and the number of calories, the nutritional value, or the like of the foods are correlated with each other.

In step S37, the nutrition determination section 13 sends the food image for which nutrition determination has already been performed to the identical food determination section 22. This allows the food image for which nutrition determination has already been performed to be registered in the identical food determination section 22 for comparison with the clipped food image in step S33 in subsequent executions of the process.

In step S38, the nutrition determination section 13 notifies the user terminal 30 of the nutrition determination results. In response to the notification, the presentation section 14 of the user terminal 30 presents to the user dietary information on the user on the basis of the results of the determination made by the nutrition determination section 13.

In step S39, the presentation section 14 of the user terminal 30 allows the user to select whether or not to terminate the real-time dietary management process. If it is not selected to terminate the process, the process returns to step S31 to repeat the subsequent steps. If it is determined to terminate the process, the real-time dietary management process is terminated.

As has been described above, the real-time dietary management process allows the user to grasp in real time the amount of calorie intake, the nutrient balance, or the like accumulated for each food being eaten.

The sequence of processes discussed above may be executed by means of hardware or by means of software. In the case where the sequence of processes is executed by means of software, a program constituting the software is installed from a program storage medium onto a computer incorporating dedicated hardware, or onto a general-purpose personal computer, for example, which is capable of executing various functions when various programs are installed.

FIG. 15 is a block diagram showing an exemplary configuration of the hardware of a computer for executing the sequence of processes discussed above through a program.

In a computer 100, a CPU (Central Processing Unit) 101, a ROM (Read Only Memory) 102, and a RAM (Random Access Memory) 103 are connected to each other through a bus 104.

An input/output interface 105 is further connected to the bus 104. To the input/output interface 105, an input section 106 such as a keyboard, a mouse, and a microphone, an output section 107 such as a display and a speaker, a storage section 108 such as a hard disk drive and a non-volatile memory, a communication section 109 such as a network interface, and a drive 110 for driving a removable medium 111 such as a magnetic disk, an optical disc, a magneto-optical disk, and a semiconductor memory are connected.

In the computer 100 configured as described above, the CPU 101 loads a program stored in the storage section 108, for example, into the RAM 103 via the input/output interface 105 and the bus 104, and executes the program to perform the sequence of processes discussed above.

The program executed by the computer may be configured such that its processes are performed chronologically in accordance with the order described herein, or such that the processes are performed concurrently or at an appropriate timing when a call is made, for example.

Moreover, the program may be executed by a single computer, or may be executed in a distributed manner by a plurality of computers. Further, the program may be transferred to a remote computer for execution.

The term "system" as used herein refers to the entire apparatus formed by a plurality of devices.

The present disclosure is not limited to the embodiment described above, and may be modified in various ways without departing from the scope and spirit of the present disclosure.

The present disclosure contains subject matter related to that disclosed in Japanese Priority Patent Application JP 2011-162790 filed in the Japan Patent Office on Jul. 26, 2011, the entire contents of which are hereby incorporated by reference.

What is claimed is:

1. An information processing apparatus comprising:
   circuitry configured to
   clip, from a plurality of captured images in which food is captured, regions that include a food item to generate a plurality of food item images, the plurality of food item images including images of a plurality of different food items;
   select, after the circuitry clips the regions that include the food item to generate the plurality of food item images, a representative food item image from among the plurality of food item images based on an evaluation value, a food item image in which a food item is captured from a particular position having a higher evaluation value and being selected as the representative food item image over a food item image in which a food item is captured from another position;
   perform image analysis to determine at least one of a number of calories and a name of a food item in the representative food item image;
   provide, to a user, after performing the image analysis, dietary history information based on the determination of the at least one of the number of calories corresponding to an amount of the food item and the name of the food item in the representative food item image; and
   provide, to the user, a food log including images of the different food items from the plurality of captured images that are associated with a user selectable display format.

2. The information processing apparatus according to claim 1, wherein the circuitry is further configured to
   determine a nutrient balance of each of the different food items in the plurality of food item images; and
   concurrently present to the user results of the nutrient balance determination of the different food items consumed during a predetermined period of time made by the circuitry on a same display.

3. The information processing apparatus according to claim 1, wherein the circuitry is further configured to
   determine which of the plurality of food item images contain the plurality of different food items based on dates and times of capture of the plurality of food item images or locations of capture of the plurality of food item images.

4. The information processing apparatus according to claim 1, wherein the circuitry is further configured to
   clip the regions by detecting tableware on which each food item is served to generate the food item images.

5. The information processing apparatus according to claim 1, further comprising:
   an image capturing sensor configured to capture a plurality of different images to generate the plurality of captured images.

6. The information processing apparatus according to claim 1, wherein
   the plurality of captured images include images of food that are consumed on different days.

7. The information processing apparatus according to claim 1, wherein the circuitry is further configured to
   group the generated plurality of food item images into one or more groups, each of the one or more groups containing at least one of the food item images of an identical food item.

8. The information processing apparatus according to claim 7, wherein the circuitry is further configured to
   select a representative food item image from one or more of the one or more groups, and determine at least one of a number of calories and a name of a food item in the selected representative food item image from the one or more of the one or more groups.

9. The information processing apparatus according to claim 8, wherein the circuitry is further configured to
   select the representative food item image from the one or more of the one or more groups in accordance with an operation performed by the user.

10. The information processing apparatus according to claim 8, wherein the circuitry is further configured to
    pair all the generated food item images to group the food item images for each identical food item based on results of a determination as to whether or not two food item images forming each pair have an identical food item.

11. The information processing apparatus according to claim 1, wherein the circuitry is further configured to
    allow the user to select the user selectable display format from a plurality of different formats including one day, one week, and one month display formats.

12. The information processing apparatus according to claim 1, wherein the circuitry is configured to select the representative food item image from among the plurality of food item images based on the evaluation value that corresponds to a characteristic of the food item depicted within the representative food item image and a characteristic of the representative food item image.

13. An information processing method performed by an information processing apparatus, comprising:
    clipping by circuitry of the information processing apparatus, from a plurality of captured images in which food is captured, regions that include a food item to generate a plurality of food item images, the plurality of food item images including images of a plurality of different food items;
    selecting, by the circuitry after clipping the regions that include the food item to generate the plurality of food item images, a representative food item image from among the plurality of food item images based on an evaluation value, a food item image in which a food item is captured from a particular position having a higher evaluation value and being selected as the representative food item image over a food item image in which a food item is captured from another position;
    performing, by the circuitry, image analysis to determine at least one of a number of calories and a name of a food item in the representative food item image;
    providing to a user, by the circuitry, after performing the image analysis, dietary history information based on the determination of the at least one of the number of calories corresponding to an amount of the food item and the name of the food item in the representative food item image; and providing, to the user, a food log including images of the different food items from the plurality of captured images that are associated with a user selectable display format.

14. A non-transitory computer-readable storage medium storing a program that, when executed, causes a computer to perform a method, the method comprising: clipping, from a plurality of captured images in which food is captured, regions that include food item to generate a plurality of food item images, the plurality of food item images including images of a plurality of different food items;

selecting, after clipping the regions that include the food item to generate the plurality of food item images, a representative food item image from among the plurality of food item images based on an evaluation value, a food item image in which a food item is captured from a particular position having a higher evaluation value and being selected as the representative food item image over a food item image in which a food item is captured from another position;

performing image analysis to determine at least one of a number of calories and a name of a food item in the representative food item image;

providing, to a user, after performing the image analysis, dietary history information based on the determination of the at least one of the number of calories corresponding to an amount of the food item and the name of the food item in the representative food item image; and providing, to the user, a food log including images of the different food items from the plurality of captured images that are associated with a user selectable display format.

* * * * *